(12) United States Patent
Lee et al.

(10) Patent No.: US 11,957,514 B2
(45) Date of Patent: Apr. 16, 2024

(54) METHOD FOR DETERMINING RELATIVE POSITION BETWEEN ARRAYS OF FLEXIBLE ARRAY DEVICE

(71) Applicant: KOREA INSTITUTE OF SCIENCE AND TECHNOLOGY, Seoul (KR)

(72) Inventors: Byung Chul Lee, Seoul (KR); Dong-Hyun Kang, Seoul (KR); Shinyong Shim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 26 days.

(21) Appl. No.: 17/273,308

(22) PCT Filed: Feb. 1, 2021

(86) PCT No.: PCT/KR2021/001285
§ 371 (c)(1),
(2) Date: Mar. 4, 2021

(87) PCT Pub. No.: WO2021/251582
PCT Pub. Date: Dec. 16, 2021

(65) Prior Publication Data
US 2023/0086770 A1 Mar. 23, 2023

(30) Foreign Application Priority Data
Jun. 11, 2020 (KR) ........................ 10-2020-0070825

(51) Int. Cl.
*A61B 8/00* (2006.01)
*A61B 8/08* (2006.01)

(52) U.S. Cl.
CPC .......... *A61B 8/4483* (2013.01); *A61B 8/5207* (2013.01)

(58) Field of Classification Search
CPC .... A61K 49/223; A61K 49/221; A61B 8/481; A61B 8/085; A61B 8/0883; A61B 8/461;
(Continued)

(56) References Cited

U.S. PATENT DOCUMENTS

| | | | | |
|---|---|---|---|---|
| 5,680,863 A | * | 10/1997 | Hossack | G10K 11/32 600/459 |
| 5,913,825 A | * | 6/1999 | Watanabe | A61B 8/4281 600/459 |
| 6,424,597 B1 | | 7/2002 | Bolomey et al. | |
| 2012/0287328 A1 | * | 11/2012 | Kawai | G02B 7/102 348/E5.042 |

(Continued)

FOREIGN PATENT DOCUMENTS

| | | |
|---|---|---|
| JP | 10-042395 A | 2/1998 |
| JP | 2002-531978 A | 9/2002 |

(Continued)

OTHER PUBLICATIONS

International Search Report dated May 10, 2021 for PCT/KR2021/001285.

*Primary Examiner* — Daniel L Murphy
*Assistant Examiner* — Amie M Ndure
(74) *Attorney, Agent, or Firm* — CANTOR COLBURN LLP

(57) ABSTRACT

The present disclosure relates to a method for determining a relative position between arrays of a flexible array device. The flexible array device according to an embodiment includes a plurality of arrays arranged at a predetermined interval in a deformable substrate, and the method includes measuring the first capacitance between adjacent arrays, measuring the second capacitance between the adjacent arrays after deformation of the substrate, and determining a relative position between the adjacent arrays based on the first capacitance measurement value and the second capacitance measurement value. According to an embodiment, the relative position between the arrays may be determined by measuring the capacitance between the adjacent arrays of the plurality of arrays arranged in the deformable substrate and measuring a change in capacitance caused by the deformation (contraction, relaxation, bending) of the substrate.

13 Claims, 16 Drawing Sheets

(58) Field of Classification Search
CPC ....... A61B 8/463; A61B 8/5246; A61B 8/485;
A61B 8/587; A61B 8/469; A61B 8/5223;
A61B 5/113; A61B 5/6823; A61B 5/08;
A61B 8/4236; A61B 8/5207; A61B
8/4281; A61B 8/08; A61B 5/6832; A61B
8/465; A61B 8/4455; A61B 8/12; A61B
8/445; A61B 8/4444; A61B 8/488; A61B
8/4472; A61B 8/4494; G16H 50/30;
G16H 50/50; G16H 30/40; G16H 30/20;
G16H 50/20; H10N 30/06; B06B 1/0292;
G06N 20/00; G06T 7/0012; A61N 7/02;
A61N 7/00
See application file for complete search history.

(56) References Cited

U.S. PATENT DOCUMENTS

| | | | |
|---|---|---|---|
| 2013/0150725 A1 | 6/2013 | Choi | |
| 2018/0145643 A1* | 5/2018 | Lafort | H04R 19/04 |
| 2019/0310125 A1* | 10/2019 | Farmanyan | G01S 13/106 |

FOREIGN PATENT DOCUMENTS

| | | | |
|---|---|---|---|
| JP | 201110788 A | 1/2011 | |
| JP | 2017-176769 A | 10/2017 | |
| KR | 19970009499 B1 | 6/1997 | |
| KR | 10-2010-0050805 A | 5/2010 | |
| KR | 10-2012-0090170 A | 8/2012 | |
| KR | 101362378 B1 | 2/2014 | |
| KR | 101654298 B1 | 9/2016 | |

* cited by examiner

METHOD FOR DETERMINING RELATIVE POSITION BETWEEN ARRAYS OF FLEXIBLE ARRAY DEVICE

DESCRIPTION OF GOVERNMENT-FUNDED RESEARCH AND DEVELOPMENT

This research is conducted by Korea Institute of Science and Technology under the support of bio-medical technology development project (Development of ultrasonic probes and attachable devices using semiconductor technology, Project Series No. 1711105874) of the Ministry of Science and ICT.

TECHNICAL FIELD

The present disclosure relates to a method for determining a relative position between arrays of a flexible array device, and more particularly, to a method for determining a relative position of arrays by measuring a change in capacitance between adjacent arrays caused by deformation (contraction, relaxation, bending) of a deformable substrate in which the plurality of arrays is arranged.

BACKGROUND ART

An ultrasonic probe includes an array of ultrasonic transducers, and the ultrasonic transducer is configured to serve as both a transmitter to output an ultrasound beam to a region of interest and a receiver to receive the ultrasound beam reflected back from the object in the region of interest. The time of flight may be measured from the transmission/reception time of the ultrasound beam, and using this, image information of the object in the region of interest may be generated. The generated ultrasonic image information may be visualized through a display. The ultrasonic probe can image the inside of the body in a noninvasive manner and thus is widely used in the medical field.

FIG. 1A shows a cross-sectional structure of the ultrasound output device 10 according to the related art. The ultrasound output device 10 of FIG. 1A has an array structure in which a plurality of ultrasonic transducers is arranged at a predetermined interval. Each transducer array outputs an ultrasound beam, and the output ultrasound is reflected back to the device by an object (for example, organ tissues, tumors, cancer cells) positioned on the travel path. A processing device connected to the device measures the time of flight of the ultrasound beam and converts it into an image.

The ultrasound output device, as shown in FIG. 1A, includes a plurality of ultrasonic transducers arranged at a predetermined interval in a rigid substrate that does not deform, and in general, a body part to be imaged has a curved shape covered with soft skin, and the skin and the ultrasonic probe device are brought into close contact through a coupling unit 11 such as a coupling gel. However, the curve of the skin is different at each part, so even though the coupling gel is used, in some situations, it may be difficult to tightly attach the ultrasonic probe device to the skin.

FIG. 1B shows a cross-section structure of the flexible ultrasound output device 20 according to the related art, and it can be tightly attached to the skin more easily than FIG. 1A. The ultrasound output device 20 of FIG. 1B includes a plurality of ultrasonic transducers arranged at a predetermined interval in a flexible substrate that can deform arbitrarily. The flexible substrate is made of a material that can deform, such as, for example, polydimethylsiloxane (PDMS), and as opposed to the structure of FIG. 1A. The flexible substrate can be tightly attached as desired along the curve of the skin without a separate coupling unit.

The structure of the ultrasound output device (rigid) of FIG. 1A may be used as an ultrasonic probe for imaging since the reference plane R for measuring the time of flight of an ultrasound beam does not move. In contrast, the ultrasound output device (flexible) of FIG. 1B has a change in the position of the reference plane (R→R') and a change in the location of the focus to which the ultrasound beam converges (F→F') with movements of the skin or changes in the pressure applied to the contact surface between the skin and the device over time. Accordingly, as the reference for measuring the time of flight of the ultrasound beam changes, it is difficult to use in ultrasonic imaging applications.

Accordingly, to acquire an ultrasonic image using a flexible material that can deform arbitrarily, there is a need for a system for determining a relative position relative to each other with the movement of the array of ultrasonic transducers in real-time and adjust the image according to position information.

DISCLOSURE

Technical Problem

The present disclosure is directed to providing embodiments of a method for determining a relative position between each array of a flexible array device and a flexible array device using the same.

Technical Solution

In a method for determining a relative position between arrays of a flexible array device according to an embodiment, the flexible array device includes a plurality of arrays arranged at a predetermined interval in a deformable substrate, and the method includes measuring the first capacitance between adjacent arrays, measuring the second capacitance between the adjacent arrays after deformation of the substrate, and determining a relative position between the adjacent arrays based on the first capacitance measurement value and the second capacitance measurement value.

According to an embodiment, determining the relative position between the adjacent arrays may include calculating a distance between the adjacent arrays based on the first capacitance measurement value, and calculating a changed distance between the adjacent arrays by the deformation of the substrate based on the second capacitance measurement value.

According to an embodiment, the first capacitance $C_1$ may be calculated by the following Equation, and $$C_1 = \varepsilon_r \varepsilon_0 \frac{t \times L}{d}$$

the second capacitance $C_2$ may be calculated by the following Equation, $$C_2 = \varepsilon_r \varepsilon_0 \lim_{n \to \infty} \sum_{k=1}^{n} \frac{(L - 2\Delta t \cdot \sin\frac{\theta}{2} \cdot (k-1)) \times \Delta t}{d + 2\Delta t \cdot \sin\frac{\theta}{2} \cdot (k-1)}$$

where t denotes a length in a direction perpendicular to a surface of the substrate of the plurality of arrays, L denotes a length in a direction parallel to the surface of the substrate of the plurality of arrays, d denotes the distance between the adjacent arrays, θ denotes an angle between the adjacent arrays by the deformation of the substrate, and $\varepsilon_r$ and $\varepsilon_0$ represent dielectric constants of the substrate and vacuum respectively.

According to an embodiment, the dielectric constant $\varepsilon_r$ of the substrate may change depending on a material of which the substrate is made, compression or tension of the substrate, and determining the relative position between the adjacent arrays may include determining the relative position between the arrays based on the capacitance measurement value between the arrays in the compression or tension.

According to an embodiment, each of the plurality of arrays may include a first part and a second part having a smaller width than the first part, a distance between the first parts and a distance between the second parts in the adjacent arrays may be different, and the method may further include determining a bending direction of the substrate based on the capacitance between the adjacent arrays changing depending on the bending direction of the substrate.

There is provided a computer program stored in a computer-readable recording medium, for performing the method for determining a relative position between arrays of a flexible array device according to embodiments.

A flexible ultrasonic imaging apparatus according to an embodiment includes a plurality of ultrasound output units arranged in a deformable substrate to output an ultrasound to a region of interest, an ultrasound receiving unit to receive the ultrasound reflected from an object disposed in the region of interest, and a processing unit to calculate a time of flight of the ultrasound based on a difference between an output time and a reception time of the ultrasound and acquire an image of the object based on the time of flight information, wherein the processing unit may be configured to measure first capacitance between adjacent ultrasound output units, measure second capacitance between the adjacent ultrasound output units after deformation of the substrate, determine a relative position of the plurality of ultrasound output units based on the first capacitance measurement value and the second capacitance measurement value, and correct the image of the object based on the relative position of the plurality of ultrasound output units.

According to an embodiment, the processing unit may be configured to determine the relative position of the plurality of ultrasound output units by calculating a distance between the adjacent arrays based on the first capacitance measurement value, and calculating a changed distance between the adjacent arrays by the deformation of the substrate based on the second capacitance measurement value.

According to an embodiment, the first capacitance $C_1$ may be calculated by the following Equation, and $$C_1 = \varepsilon_r \varepsilon_0 \frac{t \times L}{d}$$

the second capacitance $C_2$ may be calculated by the following Equation, $$C_2 = \varepsilon_r \varepsilon_0 \lim_{n \to \infty} \sum_{k=1}^{n} \frac{(L - 2\Delta t \cdot \sin\frac{\theta}{2} \cdot (k-1)) \times \Delta t}{d + 2\Delta t \cdot \sin\frac{\theta}{2} \cdot (k-1)}$$

where t denotes a length in a direction perpendicular to a surface of the substrate of the plurality of arrays, L denotes a length in a direction parallel to a surface of the substrate of the plurality of arrays, d denotes the distance between the adjacent arrays, e denotes an angle between the adjacent arrays by the deformation of the substrate, and $\varepsilon_r$ and $\varepsilon_0$ represent dielectric constants of the substrate and vacuum respectively.

According to an embodiment, the dielectric constant $\varepsilon_r$ of the substrate may change a material of which the substrate is made, compression or tension of the substrate, and the processing unit may determine the relative position between the arrays based on the capacitance measurement value between the arrays in the compression or tension.

According to an embodiment, the substrate may include at least two material layers having different dielectric constants, the capacitance may be differently measured for each material layer in the adjacent arrays, and the processing unit may be further configured to determine a bending direction of the substrate based on the capacitance between the adjacent arrays changing depending on the bending direction of the substrate.

According to an embodiment, each of the plurality of ultrasound output units may include a Micromachined Ultrasonic Transducer (MUT) and a support array to support the Micromachined Ultrasonic Transducer, the support array may include a first part and a second part having a smaller width than the first part, a distance between the first parts and a distance between the second parts in the adjacent arrays may be different, and the processing unit may be further configured to determine a bending direction of the substrate based on the capacitance between the adjacent arrays changing depending on the bending direction of the substrate.

Advantageous Effects

According to an embodiment of the present disclosure, a change in capacitance between adjacent arrays of the plurality of arrays arranged in the substrate caused by deformation (contraction, relaxation, bending) of a flexible substrate that can deform is measured. The capacitance measurement value may be used to determine a relative position between the arrays since it changes depending on the distance between the arrays and the angle between the arrays.

The method according to an embodiment may be applied to, for example, a variety of flexible devices including ultrasonic imaging systems including flexible substrates and ultrasonic transducer arrays, ultrasound treatment systems for determining the location of the focus of focused ultrasound, sensors attached to the human body to measure changes in curvature, systems for controlling interfaces according to changes in curvature and tactile sensors, and technology using the same.

DETAILED DESCRIPTION

Figure 1A:
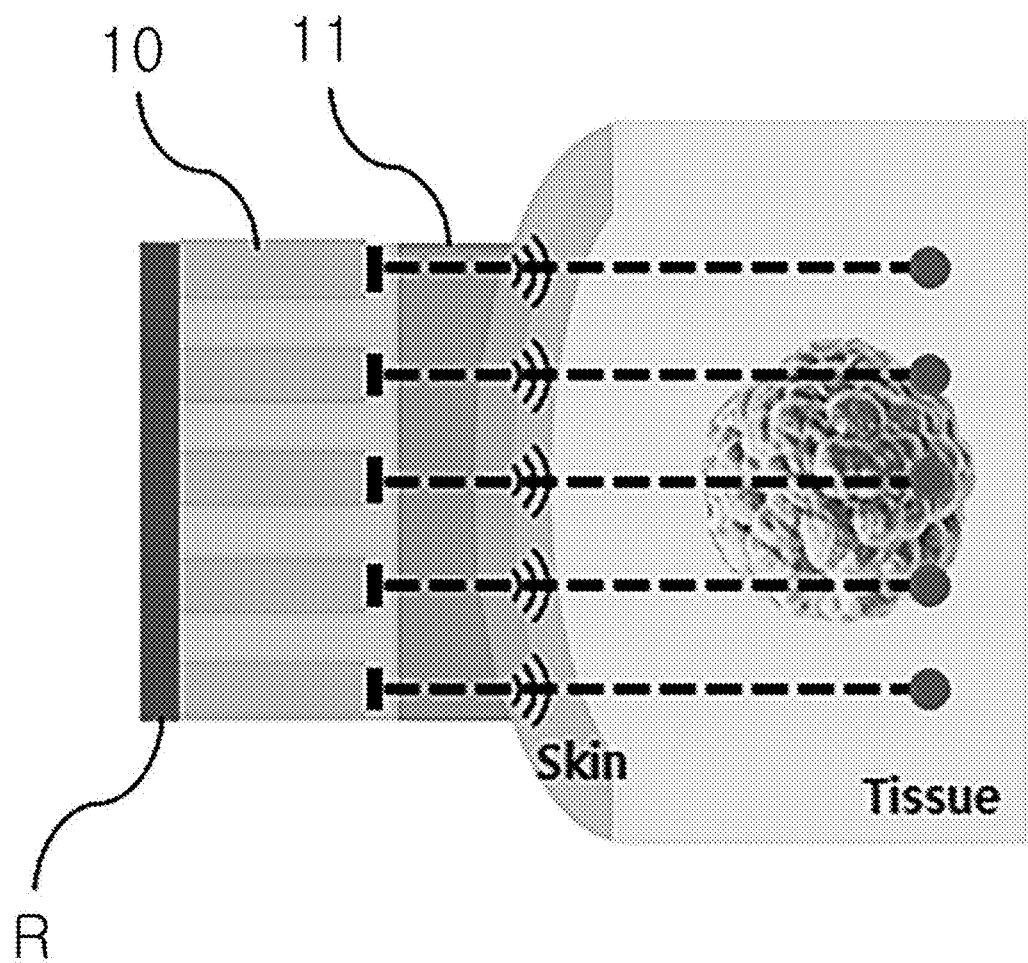
FIG. 1A shows a cross-sectional structure of an array device including a rigid substrate and ultrasonic imaging using the same.
Figure 1B:
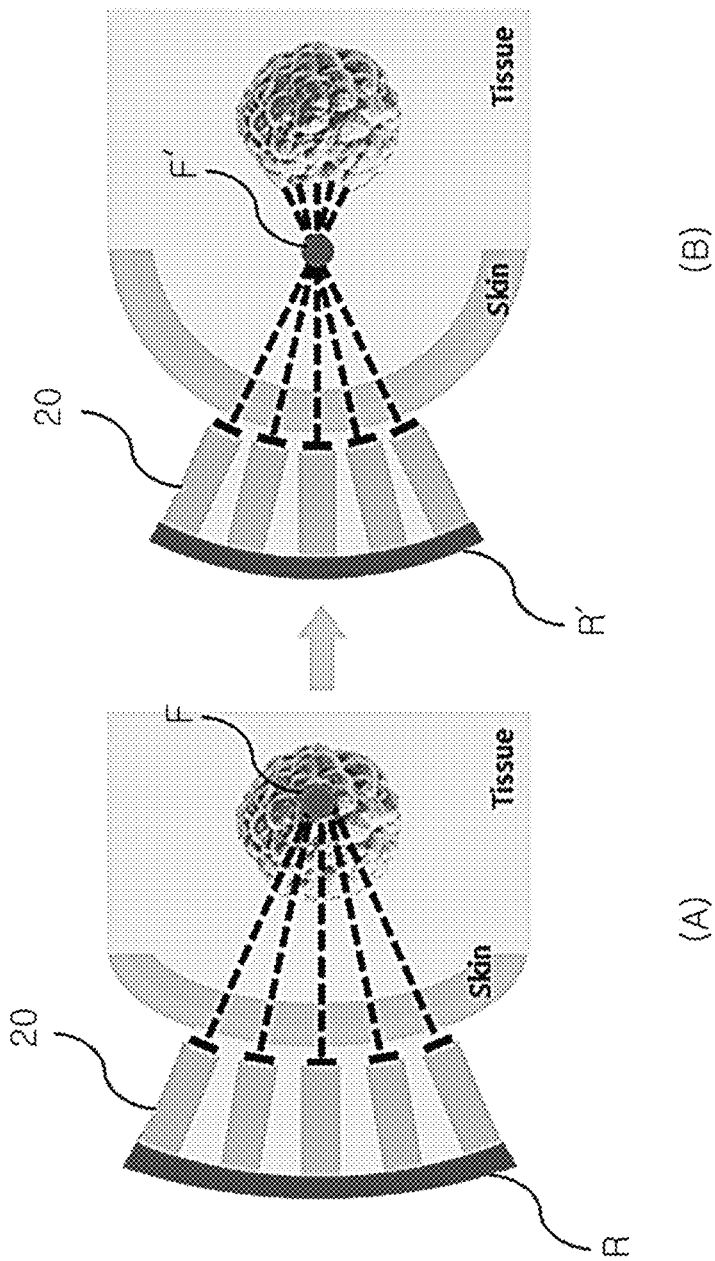
FIG. 1B shows a cross-sectional structure of an array device including a flexible substrate, and a change in reference plane and focus location with a change in a curved surface.

The following detailed description of the present disclosure is made with reference to the accompanying drawings, in which particular embodiments for practicing the present disclosure are shown for illustration purposes. These embodiments are described in sufficient detail for those skilled in the art to practice the present disclosure. It should be understood that various embodiments of the present disclosure are different but do not need to be mutually exclusive. For example, particular shapes, structures, and features described herein in connection with one embodiment can be embodied in other embodiment without departing from the spirit and scope of the present disclosure. It should be further understood that changes can be made to positions or placement of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote the same or similar functions in many aspects.

Hereinafter, the embodiments will be described in detail with reference to the accompanying drawings, but the scope of protection is not limited or restricted by the embodiments.

Figure 2:
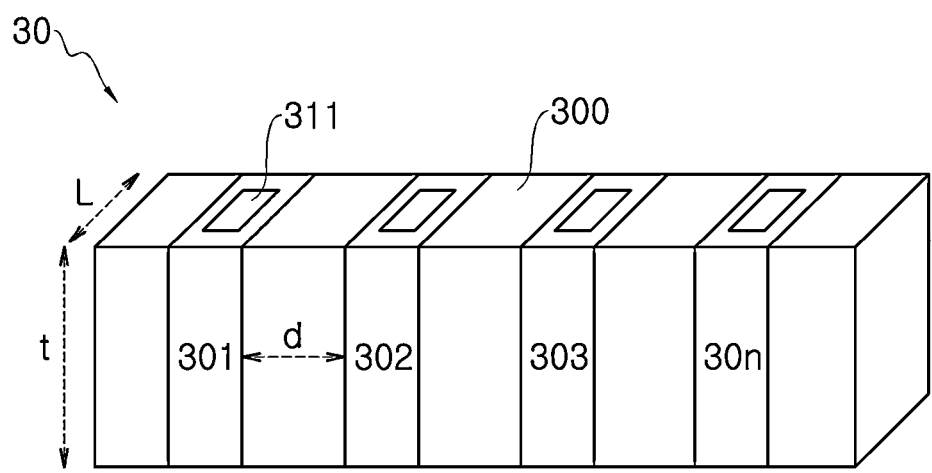
FIG. 2 is a perspective view showing the structure of a flexible array device according to an embodiment.

Method for Determining a Relative Position Between Arrays of a Flexible Array Device FIG. 2 shows the structure of a flexible array device according to an embodiment. The flexible array device 30 may include a deformable substrate 300 and a plurality of arrays 301, 302, 303, . . . 30n arranged at a predetermined interval in the substrate 300. The device may be manufactured in a suitable form for the objective and purpose and include additional components. For example, as shown in FIG. 2, a micromachined ultrasonic transducer 311 may be positioned for each array and used as an ultrasonic imaging probe or focused ultrasound treatment equipment.

According to an embodiment, the flexible array device 30 may be manufactured by placing ultrasonic transducers (for example, micromachined ultrasonic transducers such as capacitive micromachined ultrasonic transducers (CMUTs) or piezoelectric micromachined ultrasonic transducers (PMUTs)) on a silicon substrate at a predetermined interval, patterning a photoresist thereon, etching, and filling the etched area with a flexible polymer such as polydimethyl-siloxane (PDMS). The manufactured flexible array device 30 may be bent, compressed or relaxed by external forces. According to an embodiment, relative position information of each array relative to each other may be acquired by comparing the capacitance measurement values between the arrays 301, 302, 303, . . . 30n of the flexible array device.

Figure 3A:
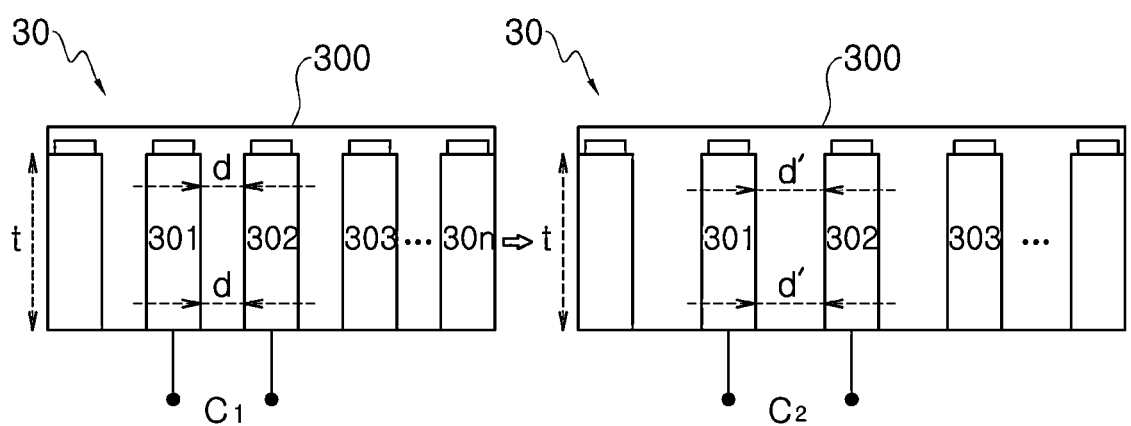
FIGS. 3A and 3B show a change in capacitance between adjacent arrays caused by deformation (stretching, bending) of a substrate in a flexible array device according to an embodiment.
Figure 3B:
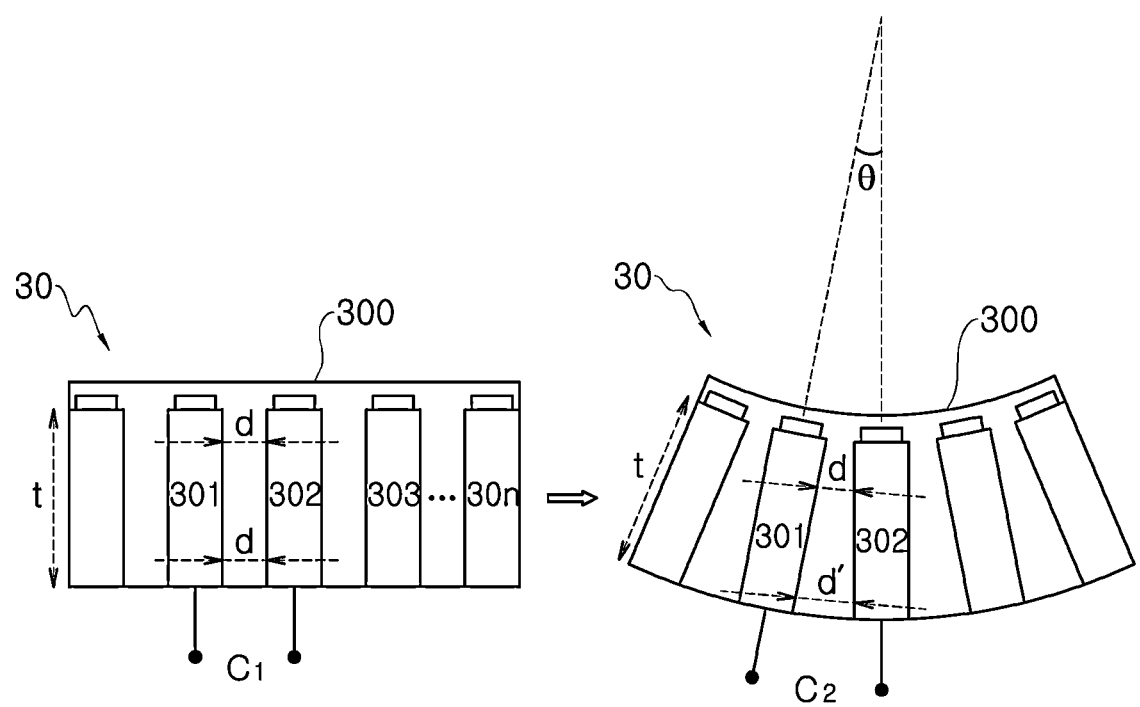

FIGS. 3A and 3B show a change in capacitance caused by deformation (stretching, bending) of the substrate in the flexible array device according to an embodiment. FIG. 3A shows the substrate stretched to the left and right, and FIG. 3B shows the substrate bent up.

Referring to FIG. 3A, first, the first capacitance $C_1$ between the adjacent arrays 301, 302 is measured in a non-deformed state of the flexible array device 30. The capacitance may be determined through a value of electric current flowing through the arrays when other variables are known. However, this is provided by way of illustration, and the capacitance may be measured through a variety of known methods in the technical field.

In this instance, the first capacitance $C_1$ may be calculated by the following Equation 1.

$$C_1 = \varepsilon_r \varepsilon_0 \frac{t \times L}{d} \quad \text{[Equation 1]}$$

Here, t denotes the length in a direction perpendicular to the upper surface of the substrate 300 of the plurality of arrays (i.e., the vertical length of the arrays), L denotes the length in a direction parallel to the surface of the substrate 300 of the plurality of arrays (i.e., the horizontal length of the arrays), and d denotes the distance between the adjacent arrays. $\varepsilon_r$ and $\varepsilon_0$ represent the dielectric constants of the substrate and vacuum, respectively.

When the actual measurement value of the first capacitance $C_1$ and the remaining variables are known, the distance d between the adjacent arrays 301, 302 may be calculated from the above Equation 1. According to an embodiment, the processing device (not shown) may be configured to receive the first capacitance measurement value in a state in which the remaining variables are inputted, and calculate the distance between the adjacent arrays in real-time.

Subsequently, after the flexible array device 30 is deformed, i.e., after the substrate 300 is stretched to the left and right, the second capacitance $C_2$ between the adjacent arrays 301, 302 is measured. As shown in FIG. 3A, when the substrate 300 is stretched to the left and right, the distance d' between the arrays 301, 302 changes, and accordingly the capacitance value between the adjacent arrays changes.

In this instance, the second capacitance $C_2$ may be calculated by the following Equation 2, and the distance d' between the arrays after the deformation may be calculated by comparing the measured first capacitance $C_1$ with the measured second capacitance $C_2$.

$$C_2 = \varepsilon_r \varepsilon_0 \frac{t \times L}{d'} \quad \text{[Equation 2]}$$

In this way, for all the other arrays 301, 302, 303, . . . 30n, relative position information of each array relative to each other may be acquired by comparing the capacitance values measured before and after the deformation of the substrate.

FIG. 3B shows a change in capacitance measured when the substrate 300 is bent. In FIG. 3A, as opposed to the substrate stretched to the left and right, the distance d' between each array is not uniform and changes depending on the extent to which the substrate is bent (i.e., the angle between the arrays). The second capacitance $C_2$ between the adjacent arrays 301, 302 after the bending of the substrate 300 may be calculated by the following Equation 3.

$$C_2 = \varepsilon_r \varepsilon_0 \lim_{n \to \infty} \sum_{k=1}^{n} \frac{(L - 2\Delta t \cdot \sin\frac{\theta}{2} \cdot (k-1)) \times \Delta t}{d' + 2\Delta t \cdot \sin\frac{\theta}{2} \cdot (k-1)} \quad \text{[Equation 3]}$$

Here, $\theta$ denotes the angle between the adjacent arrays by the deformation of the substrate 300. t denotes the length in a direction perpendicular to the upper surface of the substrate 300 of the plurality of arrays (i.e., the vertical length of the arrays), L denotes the length in a direction parallel to the surface of the substrate 300 of the plurality of arrays (i.e., the horizontal length of the arrays), and d' denotes the distance between the adjacent arrays after the deformation of the substrate. $\varepsilon_r$ and $\varepsilon_0$ are the dielectric constants of the substrate and vacuum, respectively.

Likewise, the distance between the adjacent arrays after the deformation of the substrate may be calculated by comparing the first capacitance $C_1$ with the second capacitance $C_2$, and for all the other arrays 301, 302, 303, ... 30n, a relative position of each array relative to each other may be determined by measuring a change in capacitance.

Figure 4A:
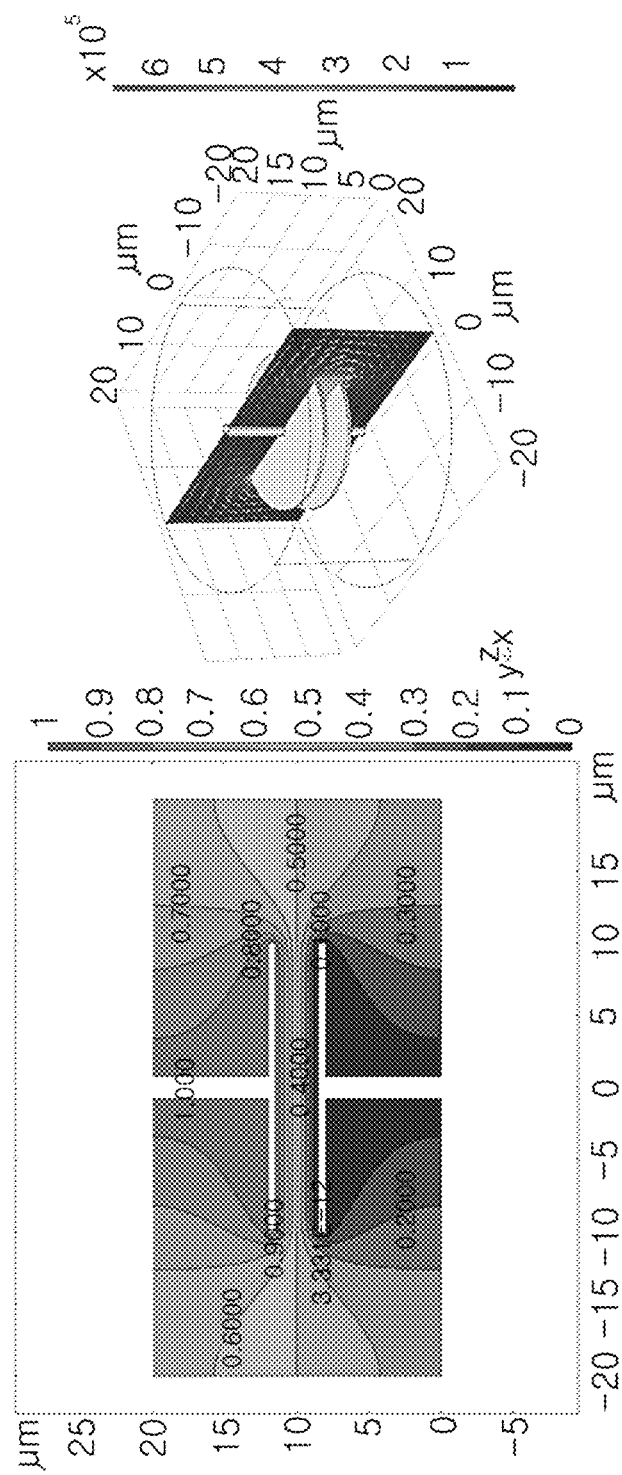
FIGS. 4A and 4B show simulation results of capacitance changing depending on an angle between adjacent arrays.
Figure 4B:
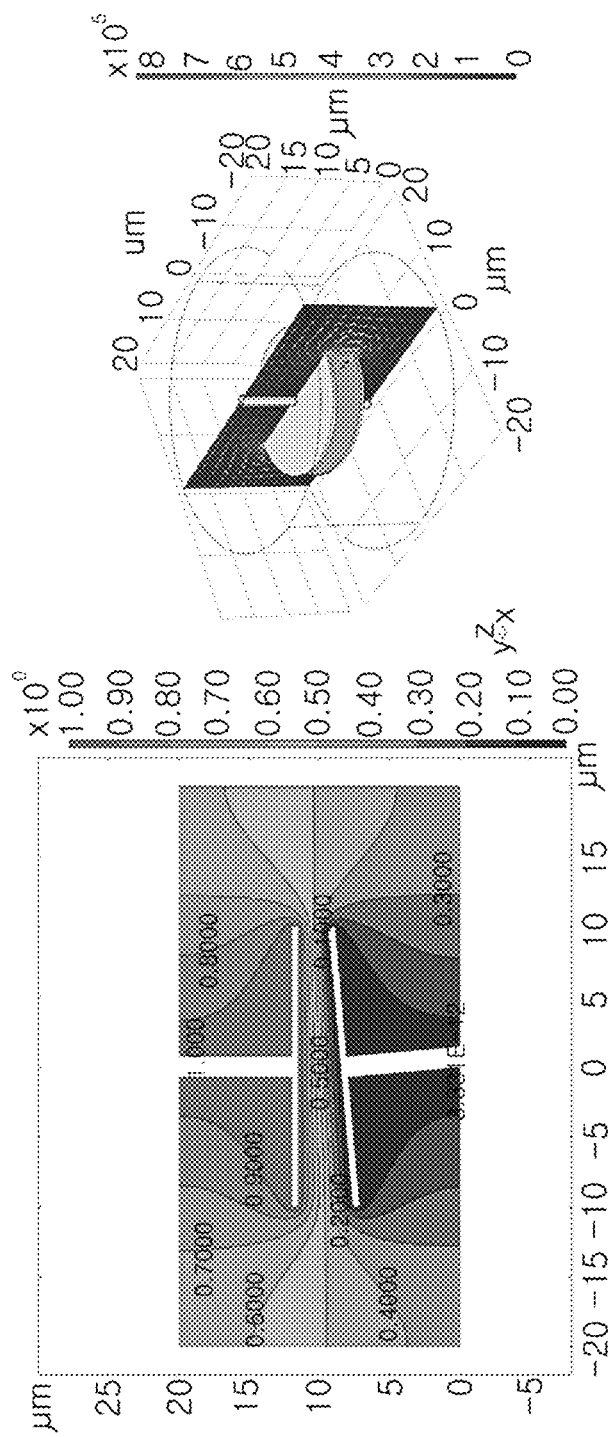

FIGS. 4A and 4B show the simulation results of the capacitance changing depending on the angle between two adjacent arrays. As shown in FIGS. 4A and 4B, the capacitance when the angle between the two arrays is 0 (i.e., the substrate is not bent and the two arrays are parallel) and the capacitance when the angle between the two arrays is 5° are differently measured. As described above, the angle and distance between the arrays may be calculated by comparing the capacitance measurement values before and after the change.

Figure 5:
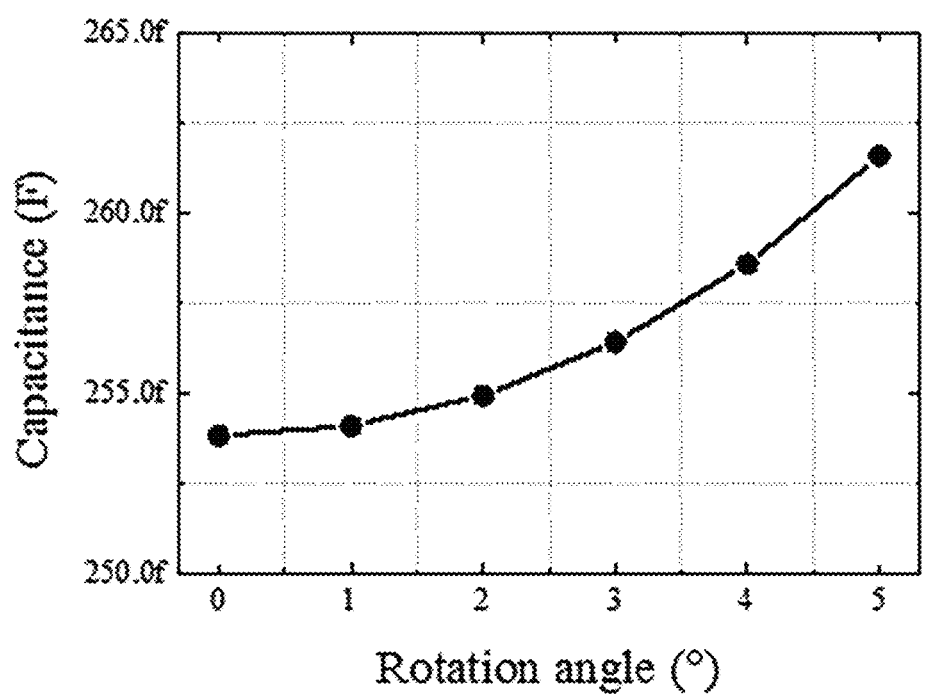
FIG. 5 is a graph showing a change in capacitance with a change in angle between adjacent arrays.

FIG. 5 is a graph showing a change in capacitance with a change in angle between the adjacent arrays. As shown, it can be seen that when the angle between the arrays changes, the capacitance value measured between the arrays changes, and the angle between the arrays may be calculated by comparing the capacitance measurement values before and after the change.

Figure 6A:
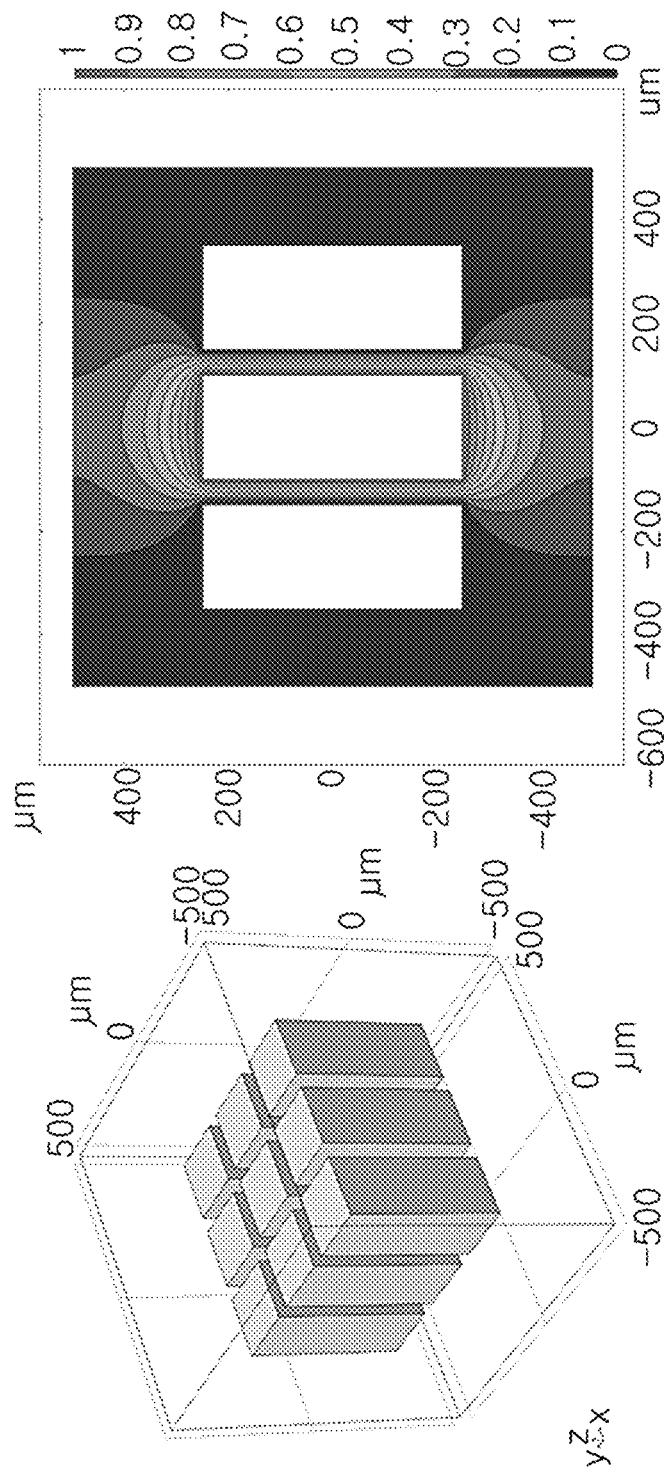
FIGS. 6A to 6C show simulation results of capacitance changing depending on the pressure applied to a flexible array device according to an embodiment.
Figure 6B:
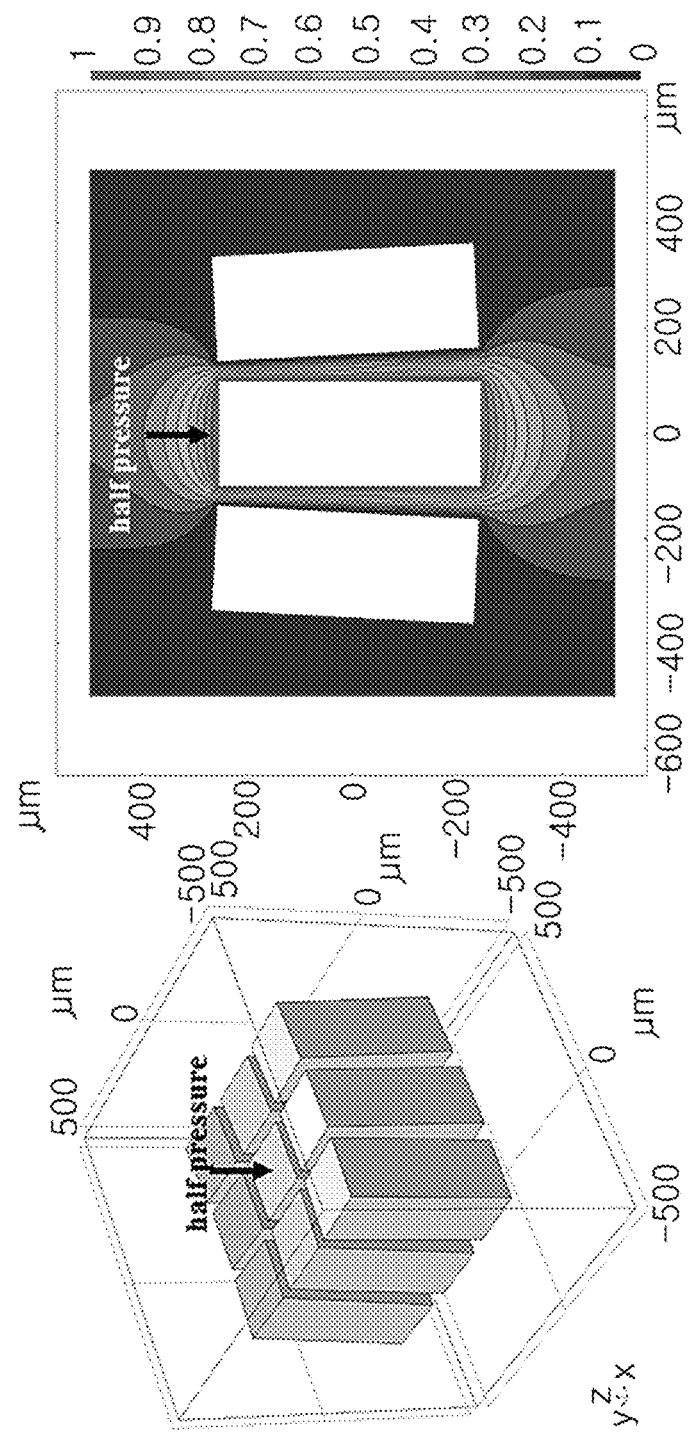
Figure 6C:
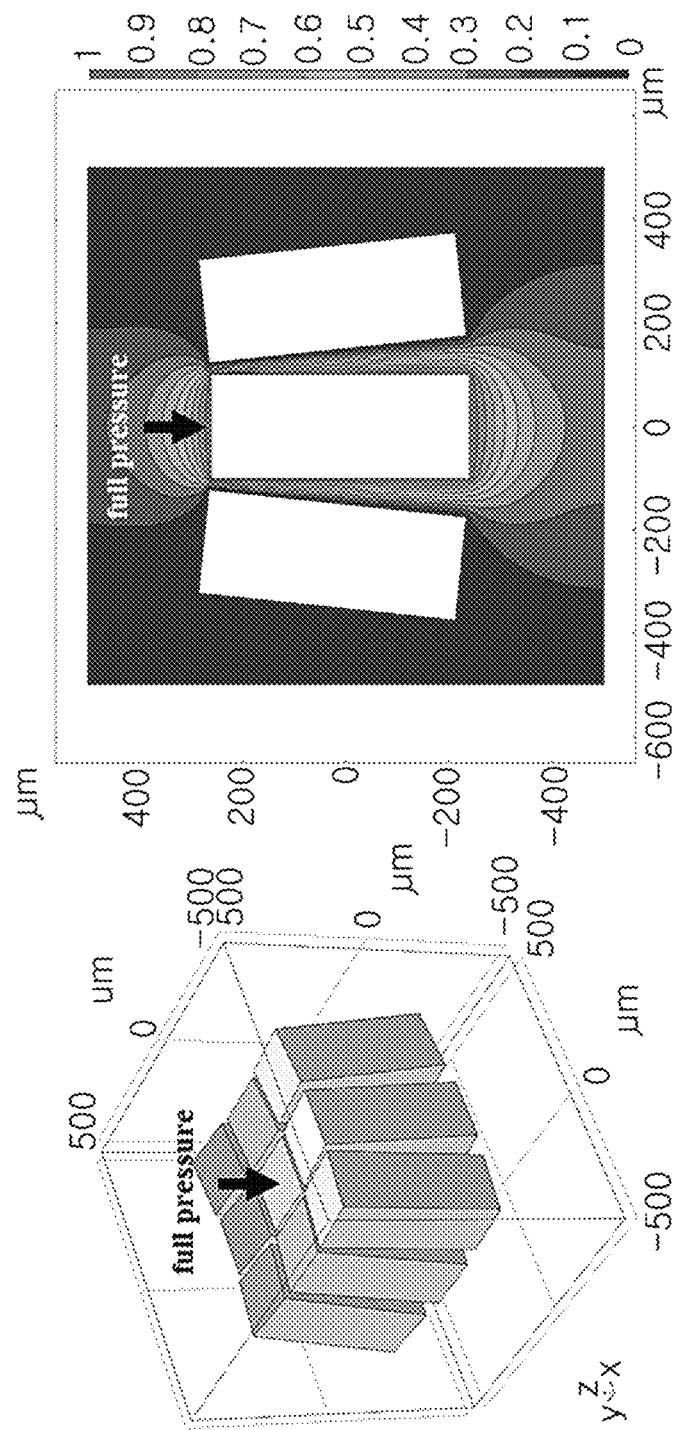

FIGS. 6A to 6C show the simulation results of the capacitance changing depending on the pressure applied to the flexible array device according to an embodiment. Each array arranged in the deformable substrate in 2D array changes in position relative to each other when the pressure is applied to the substrate, and relative position information of the arrays may be acquired by comparing the capacitance measurement values between each array before and after the deformation. As shown in FIGS. 6A and 6B, it can be seen that when the pressure is not applied to the substrate, the arrays keep parallel to each other, and when the pressure is applied to the substrate, the angle between the arrays changes and the capacitance value between the arrays changes. As shown in FIG. 6C, It can be seen that when a higher pressure is applied to the substrate, the angle between the arrays increases and accordingly the capacitance value between the arrays changes.

Figure 7:
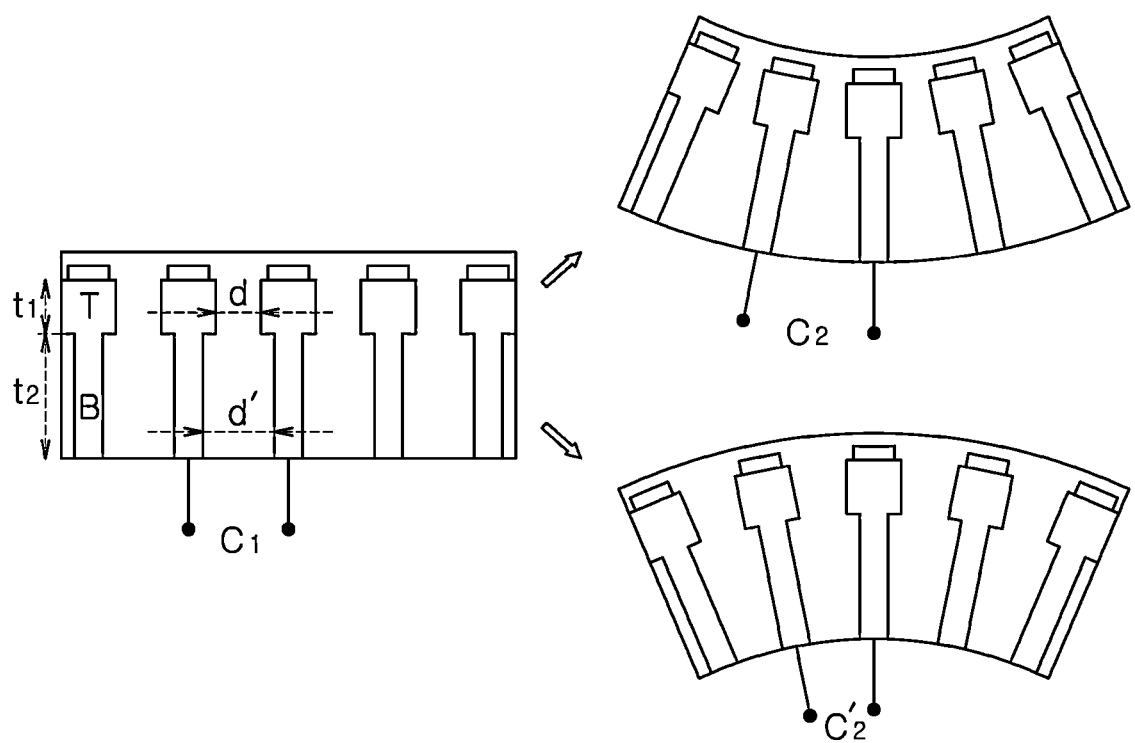
FIG. 7 shows a change in capacitance between adjacent arrays depending on a bending direction of a substrate in a flexible array device according to an embodiment.

FIG. 7 shows the capacitance between the adjacent arrays changing depending on the bending direction of the substrate in the flexible array device according to an embodiment. When the thickness of the arrays is equal over all areas, as shown in FIGS. 3A and 3B, the capacitance changes depending on the bending extent of the substrate irrespective of the bending direction of the substrate. That is, there is no change between the capacitance when the substrate is bent up and the capacitance when the substrate is bent down.

In contrast, when each array includes a first part T and a second part B having a smaller width than the first part as shown in FIG. 7, the distance d between the first parts T and the distance d' between the second parts B of each array are different and thus the capacitance measurement value between the adjacent arrays changes depending on the bending direction of the substrate. In other words, when the thickness of the arrays is different for each zone, the capacitance changes depending on the bending direction of the substrate (i.e., $C_2$ and $C_2$' are different) and thus the bending direction of the substrate may be determined therefrom.

Figure 8:
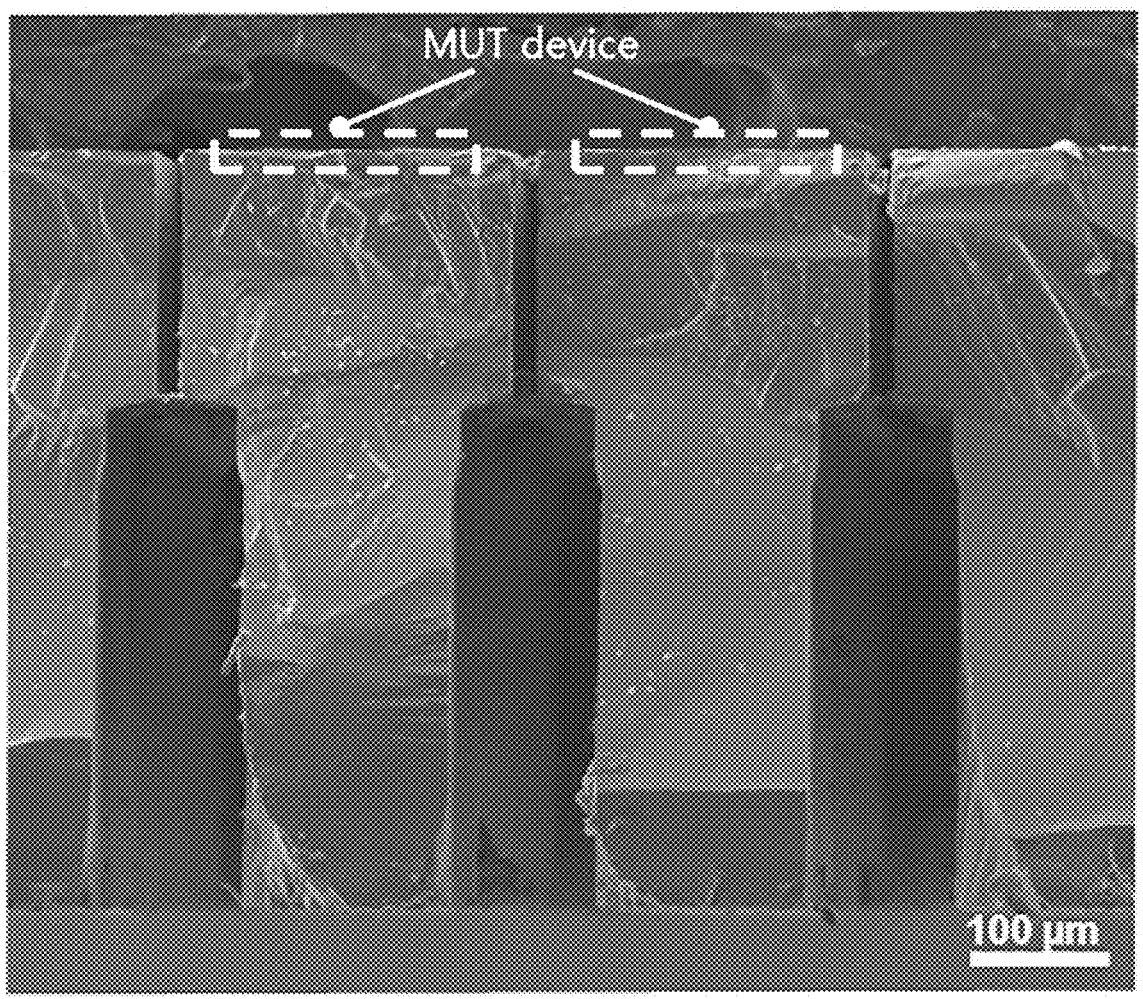
FIG. 8 is an electron microscopy image of a cross-sectional structure of a flexible array device according to an embodiment.

FIG. 8 is a scanning electron microscopy image of the cross-sectional structure of the flexible array device according to the above-described embodiment. Each array is divided into the first part and the second part having a smaller width, and there is a change in the capacitance measurement value between the arrays caused by the deformation (bending, compression/relaxation) of the substrate, and thus a relative position between the arrays or the bending direction of the substrate may be determined.

Figure 9A:
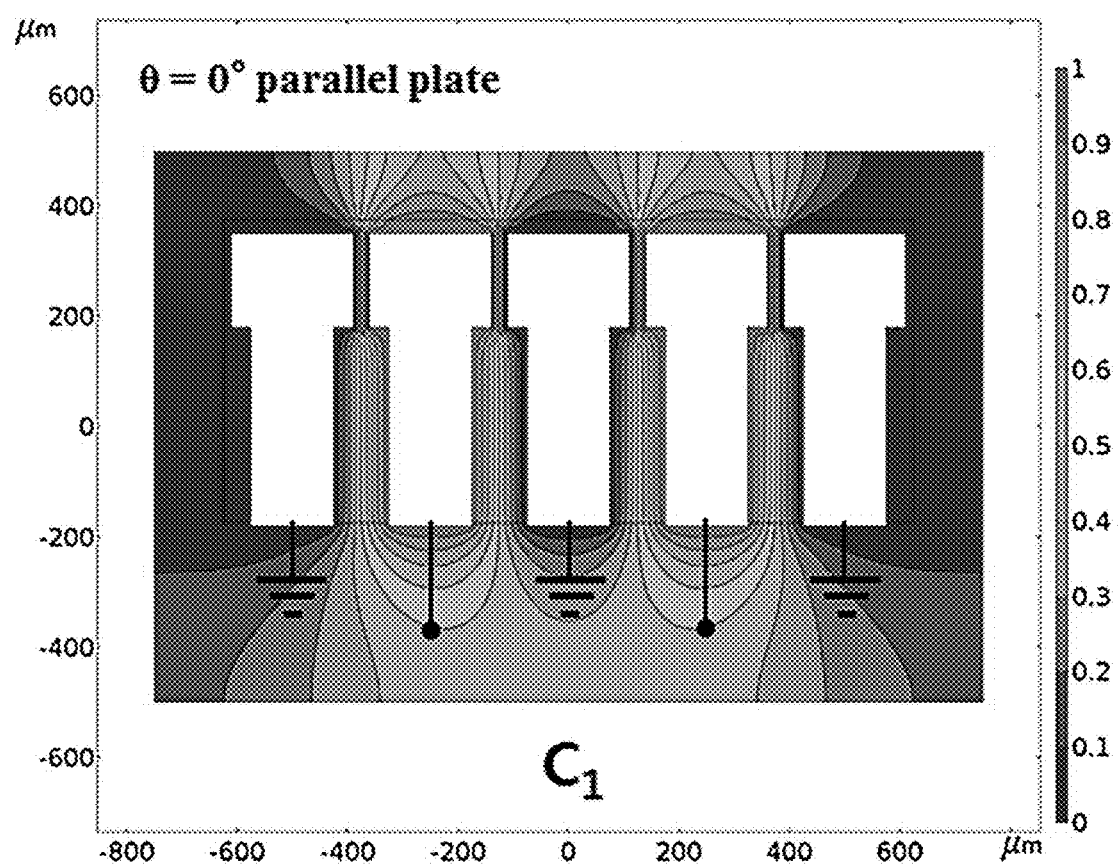
FIGS. 9A to 9C show simulation results of the capacitance changing depending on a bending direction of a substrate in a flexible array device according to an embodiment.
Figure 9B:
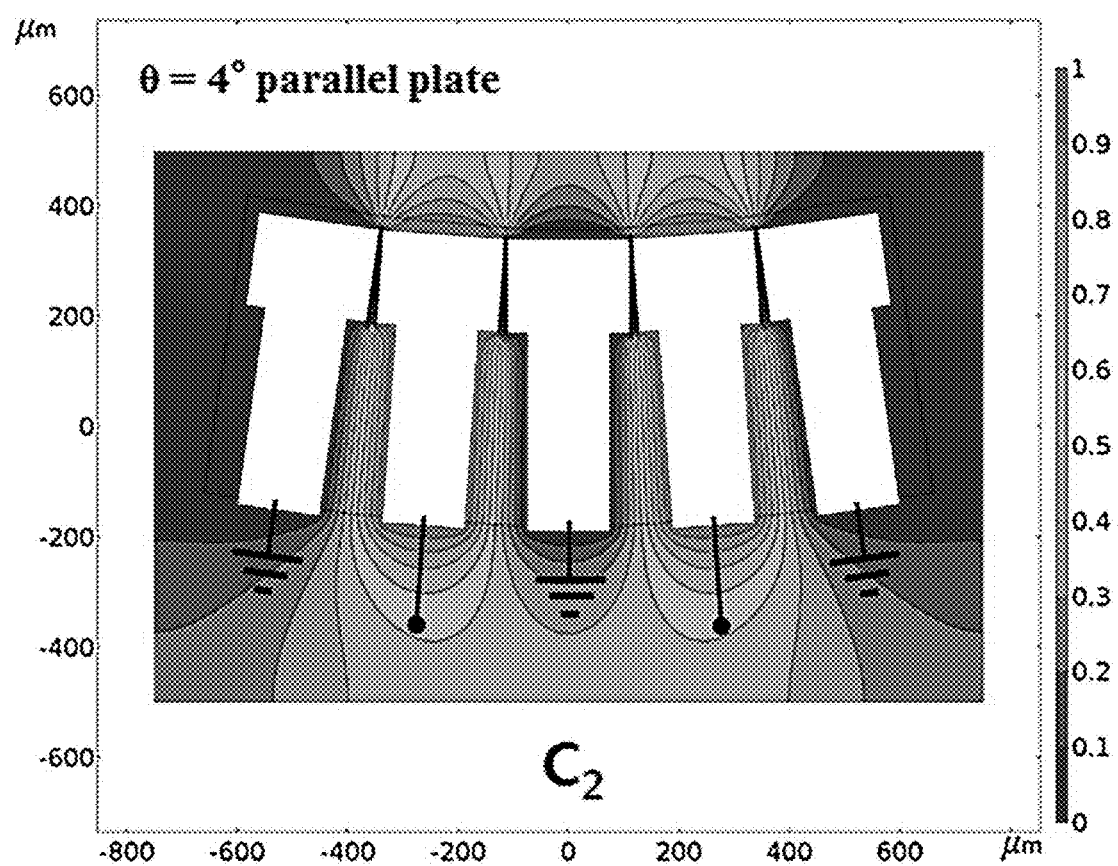
Figure 9C:
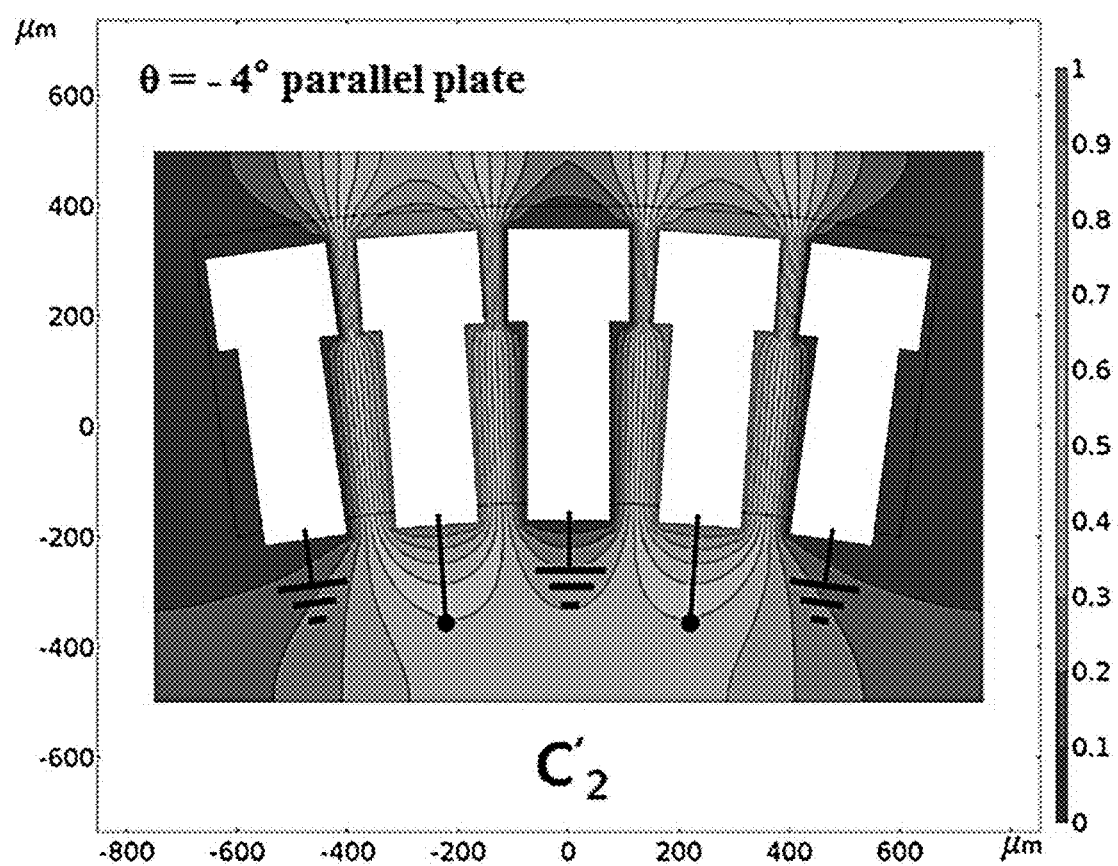

FIGS. 9A to 9C show the simulation results of the capacitance changing depending on the bending direction of the substrate in the flexible array device according to an embodiment. When each array includes the first part and the second part having a smaller width than the first part, as shown in FIGS. 9A to 9C, it can be seen that even though the extent of bending of the substrate is equal ($\theta=4°$), the capacitances $C_2$, $C_2$' have different values depending on the bending direction of the substrate. Accordingly, the relative position between the arrays and the bending direction of the substrate are identified based on the change in the capacitance measurement value.

In the equation and the simulation, it is assumed that the dielectric constant $\varepsilon_r$ of the material of the flexible substrate 300 has independently a uniform constant value in each of compression and tension, but the dielectric constant $\varepsilon_r$ may change with compression and tension depending on the material of the substrate 300 used in practice. Through this, a relative position between each array may be determined through the capacitance measurement value between the arrays in each of compression and tension.

According to an embodiment, the substrate 300 may include at least two material layers having different dielectric constants. In this case, the capacitance is differently measured for each material layer in the adjacent arrays. That is, the capacitance between the adjacent arrays is different depending on the bending direction of the substrate 300, and thus using this, the bending direction of the substrate may be determined.

Figure 10:
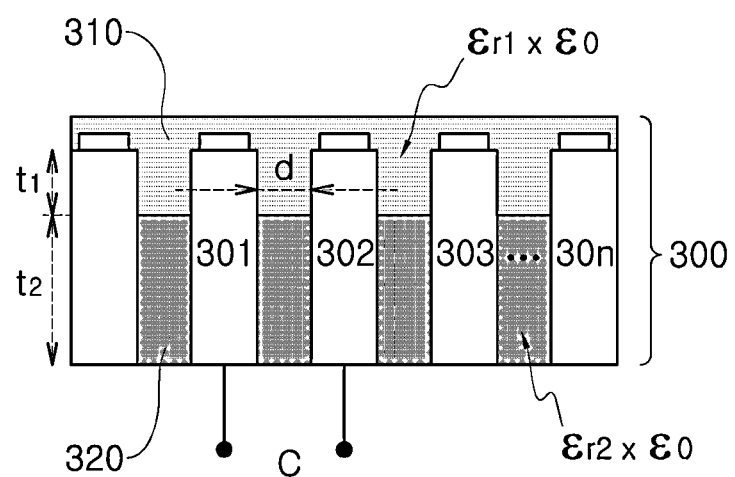
FIG. 10 shows a substrate made of materials having different dielectric constants in a flexible array device according to an embodiment.

For example, when the substrate 300 includes a first material layer 310 and a second material layer 320 having different dielectric constants, as shown in FIG. 10, the distance d between the arrays 301, 302, 303, ... 30n is equal in the first material layer 310 part and the second material layer 320 part, but due to the different dielectric constants for each material layer, the capacitance value between the adjacent arrays is differently measured from each other. That is, when the substrate 300 is bent up and when the substrate 300 is bent down, the capacitance measurement value changes (in contrast, when the substrate is made of a single material, the capacitance only changes depending on the extent of bending of the substrate irrespective of the bending direction of the substrate). Since the dielectric constant of the substrate material is known and the capacitance value can be identified from the distance between each array, the direction in which the substrate bends may be determined.

The method for determining a relative position between arrays of a flexible array device according to an embodiment may be implemented as an application or in the form of program instructions that may be executed through various computer components and may be recorded in computer-readable recording media. The computer-readable recording media may include program instructions, data files, and data structures, alone or in combination.

Examples of the computer-readable recording media include hardware devices specially designed to store and execute program instructions, for example, magnetic media such as hard disk, floppy disk and magnetic tape, optical media such as CD-ROM and DVD, magneto-optical media such as floptical disk, and ROM, RAM and flash memory.

According to the method for determining a relative position between arrays of a flexible array device as described above, the relative position between the arrays may be determined by measuring the capacitance between the adjacent arrays of the plurality of arrays arranged in the deformable substrate and measuring a change in capacitance caused by deformation (contraction, relaxation, bending) of the substrate.

Example of Specific Applications

Hereinafter, an example of specific applications using the method for determining a relative position between arrays of a flexible array device will be described.

When the method is applied to the field of ultrasonic imaging, an ultrasonic probe including an ultrasonic transducer array of a flexible material may be provided. The ultrasonic probe is a device that outputs an ultrasound beam using a plurality of ultrasonic transducer arrays, measures the time of flight of the ultrasound beam reflected by an object positioned on the traveling path and converts it into an image. To measure the time of flight of the ultrasound beam, the reference plane of the measurement needs to be invariable over time, so a substrate of a flexible material cannot be used, and accordingly it is difficult to apply to areas having a high curvature of the contact surface or frequent movements.

According to an embodiment of the present disclosure, it can be tightly attached to any body part using the flexible ultrasound output device including the array of ultrasonic transducers arranged in the deformable substrate (without the help of an ultrasound gel), and even when the position of the array of transducers changes with changes in the curvature of the contact surface or movements, it is possible to acquire an ultrasonic image by tracking a relative position of each array in real-time and reflecting on imaging process.

A flexible ultrasonic imaging apparatus according to an embodiment includes a plurality of ultrasound output units arranged in a deformable substrate to output an ultrasound to a region of interest; an ultrasound receiving unit to receive the ultrasound reflected from an object positioned in the region of interest; and a processing unit to calculate the time of flight of the ultrasound based on a difference between the output time and reception time of the ultrasound and acquire an image of the object based on the time of flight information.

The processing unit is configured to measure the first capacitance between the adjacent ultrasound output units and the second capacitance between the adjacent ultrasound output units after deformation of the substrate, determine a relative position of the plurality of ultrasound output units based on the first capacitance measurement value and the second capacitance measurement value, and correct the image of the object based on the relative position of the plurality of ultrasound output units. The capacitance measurement of each ultrasound output unit may be performed through Equations 1 to 3 as described above.

When a flexible device is tightly attached to the skin by the existing method, the reference plane for measuring the time of flight of ultrasound changes with curvature changes or movements of the skin, and thus it is difficult to acquire accurate images, but according to an embodiment, changes in the position of the arrays (ultrasonic transducer arrays) are reflected on the imaging process in real-time, thereby removing the influence of device deformation and acquiring accurate images.

According to an embodiment, each of the plurality of ultrasound output units may include a Micromachined Ultrasonic Transducer (MUT) and a support array to support the Micromachined Ultrasound Transducer, and the support array may include a first part and a second part having a narrower width than the first part. As described above, when the width of the support arrays is equal, the capacitance changes depending on the extent to which the substrate bends irrespective of the direction in which the substrate bends, but when the width of the arrays is different, the capacitance measurement value changes depending on the direction in which the substrate bends, and thus the direction in which the substrate bends can be identified. According to an embodiment, the processing unit may be further configured to determine the direction in which the substrate bends based on a difference in capacitance due to the distance between the first parts of the adjacent support arrays and the distance between the second parts of the adjacent support arrays.

Meanwhile, in the case of noninvasive ultrasonic testing for a curved structure such as a pipe, it is necessary to include each ultrasonic transducer having a curve that matches the diameter of each pipe, or to measure and correct the diameter of each pipe, but using an embodiment of the present disclosure, it can be tightly attached to the surface accurately irrespective of the type of pipes having various curves, and thus it is possible to measure the curve of the pipe, and at the same time, to measure a fault in each pipe structure via ultrasonic imaging.

Additionally, in an ultrasound treatment apparatus that directly stimulates the body part using high-intensity focused ultrasound (HIFU) or low-intensity focused ultrasound (LIFU), the existing flexible ultrasound output device changes in the focus location of the focused ultrasound with curvature changes or movements of the contact surface of the body (because the location of each transducer changes), making it difficult to accurately emit ultrasound to the desired point.

According to an embodiment of the present disclosure, it is possible to acquire relative position information of the array of ultrasonic transducers and track a change in the focus location of the focused ultrasound in real-time. Based on the position information, a user can arbitrarily control the direction and focus location of the ultrasound beam from each transducer array. Accordingly, it is possible to design with different response characteristics necessary for imaging diagnosis and treatment by further improving the intensity and resolution of the focus necessary for ultrasound imaging and treatment, respectively.

Additionally, the present disclosure may be applied to sensors that are attached to the human body to measure changes in curvature. For example, a sensor including a thin flexible substrate and a plurality of arrays may be attached to the skin, and when the skin curvature changes due to joint motion, breathing and swelling, a consequential change in capacitance between the arrays may be measured, and a change in skin curvature may be identified from a change in the relative position of the arrays. In particular, it can be used as a type of wearable device which is attached to the body parts to collect repeatedly measured data such as changes in breathing, heartbeats, and pulses.

Additionally, the present disclosure may be applied to pressure sensors for input devices, for example, keyboards, based on the idea that the position of each array device is changed by the pressing pressure. For example, the present disclosure may be used as wearable interface devices using changes in capacitance between arrays caused by depending on skin movements or pressing forces after attached to the skin.

Additionally, when the flexible array device is used to make robotic skins, it can be used as tactile sensors that can measure the pressing pressure and sense pulling or pinching situations as if it would be human skin.

While the present disclosure has been hereinabove described with reference to the embodiments, it will be understood by those having ordinary skill in the corresponding technical field that various modifications and changes may be made to the present disclosure without departing from the spirit and scope of the present disclosure as defined by the appended claims.

The invention claimed is:

1. A method for determining a relative position between arrays of a flexible array device, in which the flexible array device includes a plurality of arrays arranged at a predetermined interval in a deformable substrate, the method comprising:
measuring first capacitance between adjacent arrays;
measuring second capacitance between the adjacent arrays after deformation of the substrate; and
determining a relative position between the adjacent arrays based on the first capacitance measurement value and the second capacitance measurement value,
wherein the first capacitance $C_1$ is calculated by the following Equation, $$C_1 = \varepsilon_r \varepsilon_0 \frac{t \times L}{d}$$

where t denotes a length of each of the adjacent arrays in a direction perpendicular to an upper surface of the substrate, L denotes a length of each of the adjacent arrays in a direction parallel to the upper surface of the substrate, d denotes a distance between the adjacent arrays, and, $\varepsilon_r$ and $\varepsilon_0$ represent dielectric constants of the substrate and vacuum, respectively,
wherein the distance between the adjacent arrays is changed after the deformation of the substrate, and the second capacitance measurement value is different from the first capacitance measurement value by the change in the distance between the adjacent arrays.

2. The method for determining a relative position between arrays of a flexible array device according to claim 1, wherein determining the relative position between the adjacent arrays comprises:
calculating the distance between the adjacent arrays based on the first capacitance measurement value; and
calculating the changed distance between the adjacent arrays by the deformation of the substrate based on the second capacitance measurement value.

3. The method for determining a relative position between arrays of a flexible array device according to claim 2, wherein
the second capacitance $C_2$ is calculated by the following Equation, $$C_2 = \varepsilon_r \varepsilon_0 \lim_{n \to \infty} \sum_{k=1}^{n} \frac{(L - 2\Delta t \cdot \sin\frac{\theta}{2} \cdot (k-1)) \times \Delta t}{d + 2\Delta t \cdot \sin\frac{\theta}{2} \cdot (k-1)}$$

where θ denotes an angle between the adjacent arrays by the deformation of the substrate.

4. The method for determining a relative position between arrays of a flexible array device according to claim 3, wherein the dielectric constant $\varepsilon_r$ of the substrate changes depending on a material of which the substrate is made, compression or tension of the substrate, and
determining the relative position between the adjacent arrays comprises determining the relative position between the arrays based on the capacitance measurement value between the arrays in the compression or tension.

5. The method for determining a relative position between arrays of a flexible array device according to claim 4, wherein the substrate includes at least two material layers having different dielectric constants, and the capacitance is differently measured for each material layer in the adjacent arrays, and
the method further comprises determining a bending direction of the substrate based on the capacitance between the adjacent arrays changing depending on the bending direction of the substrate.

6. The method for determining a relative position between arrays of a flexible array device according to claim 1, wherein each of the plurality of arrays includes a first part and a second part having a smaller width than the first part, and a distance between the first parts and a distance between the second parts in the adjacent arrays are different, and
the method further comprises determining a bending direction of the substrate based on the capacitance between the adjacent arrays changing depending on the bending direction of the substrate.

7. A flexible ultrasonic imaging apparatus, comprising:
a plurality of ultrasound output units arranged in a deformable substrate to output an ultrasound to a region of interest;
an ultrasound receiving unit to receive the ultrasound reflected from an object disposed in the region of interest; and
a processing unit to calculate a time of flight of the ultrasound based on a difference between an output time and a reception time of the ultrasound and acquire an image of the object based on the time of flight information,
wherein the processing unit is configured to:
measure first capacitance between adjacent ultrasound output units,
measure second capacitance between the adjacent ultrasound output units after deformation of the substrate, determine a relative position of the plurality of ultrasound output units based on the first capacitance measurement value and the second capacitance measurement value, and correct the image of the object based on the relative position of the plurality of ultrasound output units.

8. The flexible ultrasonic imaging apparatus according to claim 7, wherein the processing unit is configured to determine the relative position of the plurality of ultrasound output units by calculating a distance between the adjacent arrays based on the first capacitance measurement value, and calculating a changed distance between the adjacent arrays by the deformation of the substrate based on the second capacitance measurement value.

9. The flexible ultrasonic imaging apparatus according to claim 8, wherein the first capacitance $C_1$ is calculated by the following Equation, and $$C_1 = \varepsilon_r \varepsilon_0 \frac{t \times L}{d}$$

the second capacitance $C_2$ is calculated by the following Equation, $$C_2 = \varepsilon_r \varepsilon_0 \lim_{n \to \infty} \sum_{k=1}^{n} \frac{(L - 2\Delta t \cdot \sin\frac{\theta}{2} \cdot (k-1)) \times \Delta t}{d + 2\Delta t \cdot \sin\frac{\theta}{2} \cdot (k-1)}$$

where t denotes a length in a direction perpendicular to a surface of the substrate of the plurality of arrays, L denotes a length in a direction parallel to a surface of the substrate of the plurality of arrays, d denotes the distance between the adjacent arrays, θ denotes an angle between the adjacent arrays by the deformation of the substrate, and $\varepsilon_r$ and $\varepsilon_0$ represent dielectric constants of the substrate and vacuum respectively.

10. The flexible ultrasonic imaging apparatus according to claim 9, wherein the dielectric constant $\varepsilon_r$ of the substrate changes a material of which the substrate is made, compression or tension of the substrate, and the processing unit determines the relative position between the arrays based on the capacitance measurement value between the arrays in the compression or tension.

11. The flexible ultrasonic imaging apparatus according to claim 10, wherein the substrate includes at least two material layers having different dielectric constants, and the capacitance is differently measured for each material layer in the adjacent arrays, and the processing unit is further configured to determine a bending direction of the substrate based on the capacitance between the adjacent arrays changing depending on the bending direction of the substrate.

12. The flexible ultrasonic imaging apparatus according to claim 7, wherein each of the plurality of ultrasound output units includes a Micromachined Ultrasonic Transducer (MUT) and a support array to support the Micromachined Ultrasonic Transducer, the support array includes a first part and a second part having a smaller width than the first part, and a distance between the first parts and a distance between the second parts in the adjacent arrays are different, and the processing unit is further configured to determine a bending direction of the substrate based on the capacitance between the adjacent arrays changing depending on the bending direction of the substrate.

13. A computer program stored in a computer-readable recording medium, for performing the method for determining a relative position between arrays of a flexible array device according to claim 1.

* * * * *